(12) United States Patent
Drake et al.

(10) Patent No.: US 9,927,422 B2
(45) Date of Patent: Mar. 27, 2018

(54) METHOD AND DEVICE FOR MEASURING DENTIN PERMEABILITY

(71) Applicant: The Procter & Gamble Company, Cincinnati, OH (US)

(72) Inventors: Phillip Asa Drake, Mason, OH (US); Tiffany Celeste Hare, West Chester, OH (US); John Patrick Herlinger, Germantown, OH (US); Richard Craig Maupin, Okeana, OH (US)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 446 days.

(21) Appl. No.: 14/276,090

(22) Filed: May 13, 2014

(65) Prior Publication Data

US 2015/0330966 A1 Nov. 19, 2015

(51) Int. Cl.
*G01N 15/08* (2006.01)
*G01N 33/50* (2006.01)
*G01N 33/483* (2006.01)
*G01F 1/00* (2006.01)

(52) U.S. Cl.
CPC ....... *G01N 33/502* (2013.01); *G01N 15/0826* (2013.01); *G01N 33/4833* (2013.01); *G01F 1/007* (2013.01)

(58) Field of Classification Search
CPC ............. G01N 33/502; G01N 33/4833; G01N 15/0826
See application file for complete search history.

(56) References Cited

U.S. PATENT DOCUMENTS

| | | | |
|---|---|---|---|
| 5,597,552 A | 1/1997 | Herms et al. | |
| 6,506,055 B1 | 1/2003 | Pashley et al. | |
| 9,128,020 B2 * | 9/2015 | Heipp | G01N 15/0806 |
| 9,134,217 B2 * | 9/2015 | Sharma | G01N 15/08 |
| 9,134,219 B2 * | 9/2015 | Heipp | G01N 15/0826 |
| 2002/0041852 A1 | 4/2002 | Napolitano et al. | |
| 2007/0098652 A1 * | 5/2007 | Chow | A61K 8/19 424/52 |
| 2009/0186090 A1 * | 7/2009 | Zaidel | A61K 8/25 424/489 |
| 2010/0322984 A1 | 12/2010 | Rees et al. | |
| 2012/0027828 A1 | 2/2012 | Kleinberg et al. | |
| 2014/0060156 A1 | 3/2014 | Heipp et al. | |
| 2014/0060158 A1 * | 3/2014 | Heipp | G01N 15/0806 73/38 |
| 2014/0060159 A1 | 3/2014 | Sharma et al. | |
| 2014/0090977 A1 * | 4/2014 | Boardman | G01N 27/404 204/415 |

(Continued)

FOREIGN PATENT DOCUMENTS

WO     WO0059460     10/2000

OTHER PUBLICATIONS

In Vitro Dentin Permeability After Application of Gluma Desensitizer as Aqueous Solution or Aqueous Fumed Silica Dispersion; Ishihata, Hiroshi, Finer Wener J., Kanehira, Masafumi, Shimauchi, Hidetoshi, Komatsu, Masashi; Journal Applied Oral Science ; 2011:19(2) pp. 147-153.

*Primary Examiner* — Ralph Lewis

(57) ABSTRACT

A method and device for visually recording hydraulic conductance through a sectioned piece of dentin; and which can be used to measure the effectiveness of treatments to reduce the permeability of dentin.

5 Claims, 10 Drawing Sheets

(56) References Cited

U.S. PATENT DOCUMENTS

| | | | |
|---|---|---|---|
| 2015/0118166 A1* | 4/2015 | Sagel | A61K 8/362 424/49 |
| 2015/0202128 A1* | 7/2015 | Saito | A61K 8/24 424/57 |
| 2016/0067167 A1* | 3/2016 | Prosise | A61Q 11/00 424/50 |

* cited by examiner

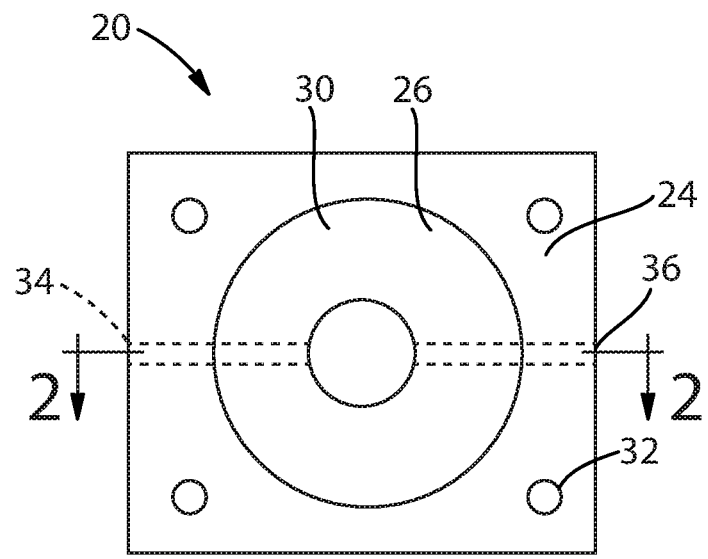
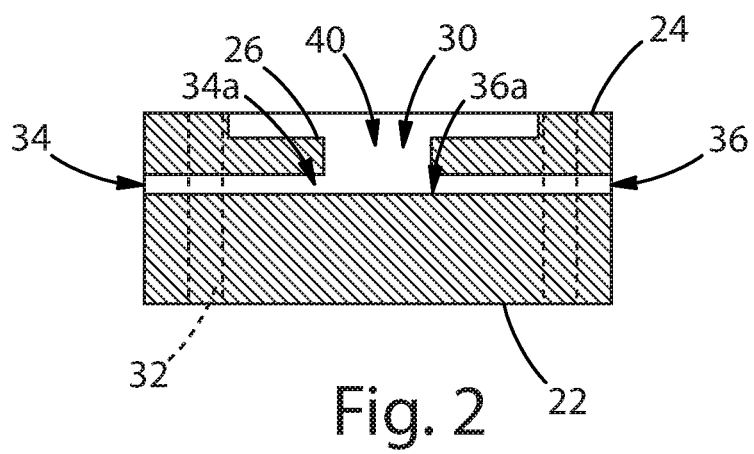

Frame sequence showing progressive appearance of liquid atop an untreated dentin surface. Pressure was applied at time = 0 s at 5 pounds per square inch.

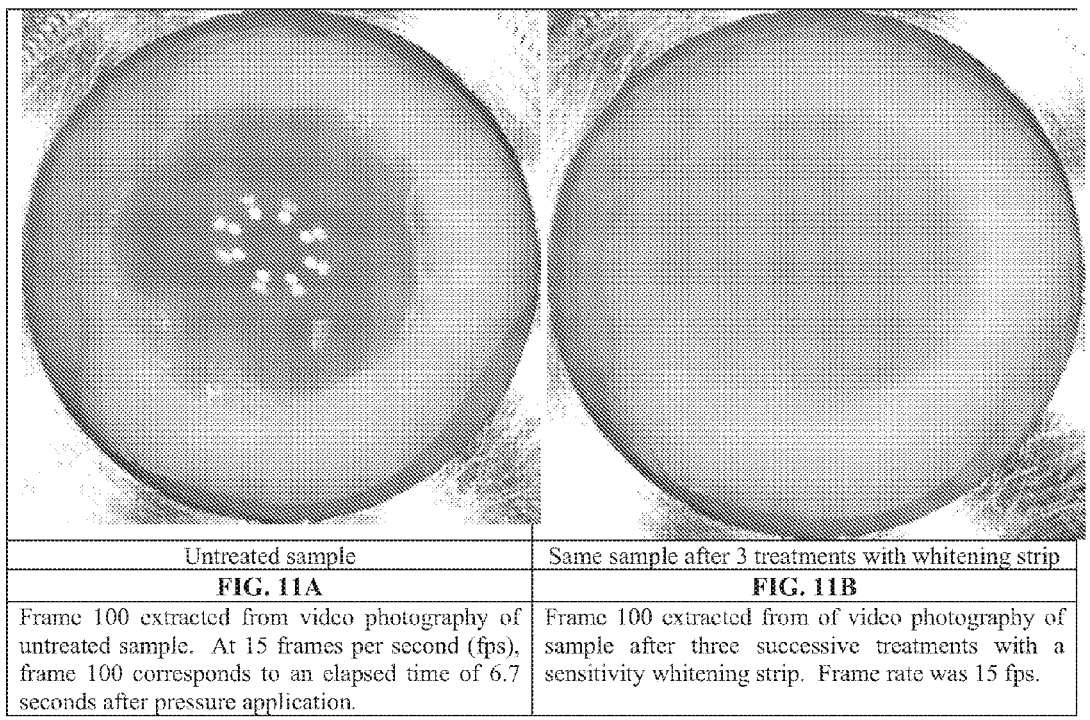

| Untreated sample | Same sample after 3 treatments with whitening strip |
|---|---|
| FIG. 11A | FIG. 11B |
| Frame 100 extracted from video photography of untreated sample. At 15 frames per second (fps), frame 100 corresponds to an elapsed time of 6.7 seconds after pressure application. | Frame 100 extracted from of video photography of sample after three successive treatments with a sensitivity whitening strip. Frame rate was 15 fps. |

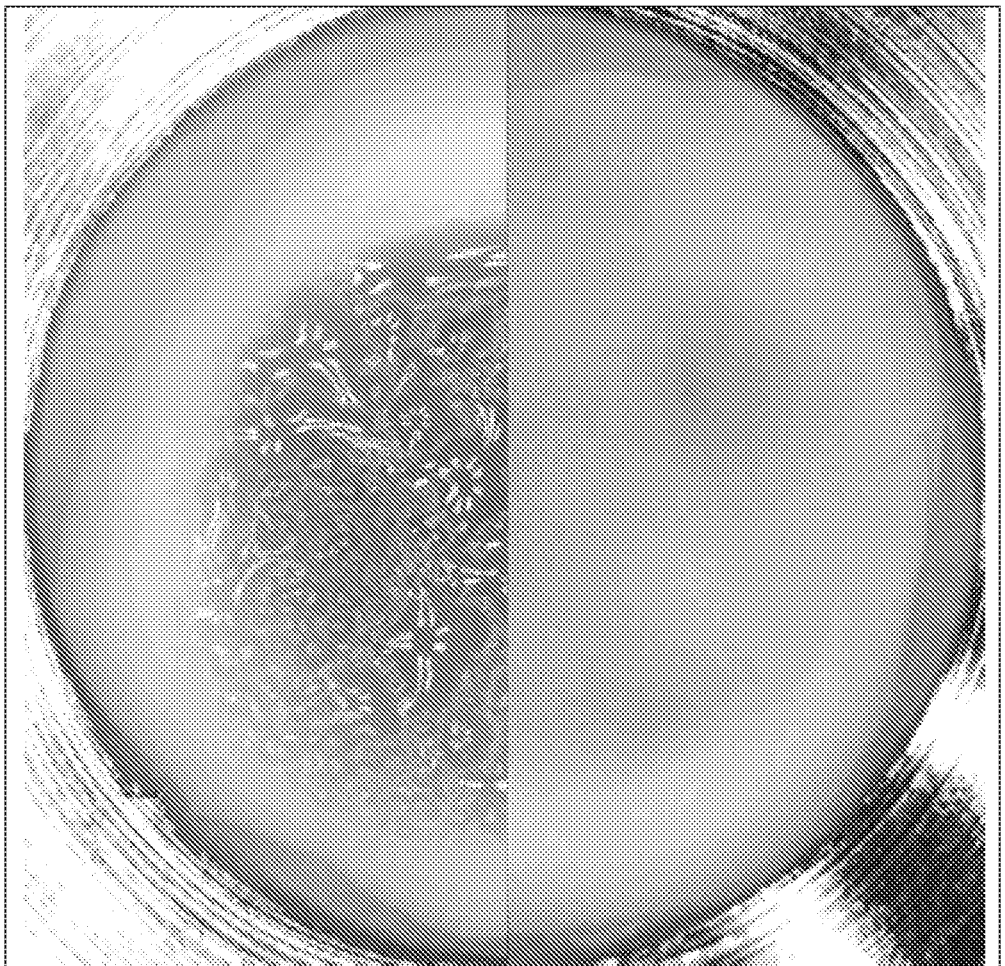

FIG. 12

Cropped overlay from video photography of dentin after 3 treatment cycles with a test dentifrice (left) and 3 treatment cycles with a sensitivity strip (right). In each case frame 22 was extracted from video collected at 15 fps, in which pressure was applied simultaneously with capture of the 1st frame. Virtual dub software was used to crop videos in preparation for overlay.

METHOD AND DEVICE FOR MEASURING DENTIN PERMEABILITY

FIELD OF THE INVENTION

The invention relates to a method and device that allows visual recordation of hydraulic conductance through a sectioned piece of dentin; and which can be used to measure the effectiveness of treatments to reduce the permeability of dentin.

BACKGROUND OF THE INVENTION

A large portion of US households (60%) have at least one family member that suffers from hypersensitive teeth. Products, such as toothpaste, targeting consumers suffering from tooth sensitivity are the fastest growing segment of the oral care market; however, the results provided by sensitivity toothpastes leave a majority of users (60%) unsatisfied, with 57% of sufferers willing to try products other than toothpaste.

Tooth sensitivity can be activated by hot and cold drinks and certain acidic or hypertonic foods. This sensitivity often occurs when gum tissue recedes from the necks of teeth, exposing root surfaces that are not covered by hard enamel but by soft cementum. The cementum is so thin and soft that it can be removed by tooth brushing, thereby exposing the sensitive underlying dentin. The dentin can also become exposed under restorations. The pain that patients feel from exposed dentin is called dentin sensitivity, as reported in Pashley, Arch Oral Biol 39 (Suppl) 735-805 (1994).

Dentin sensitivity, whether on exposed surfaces at the necks of teeth or under restorations, is reportedly due to minute fluid shifts across dentin in response to painful stimuli (Brannstrom, Oper Dent 9: 59-68, 1984). This theory, called the hydrodynamic theory, (Brannstrom and Astrom, Int Dent J 22: 219-j226, 1972), assumes that fluid can move within or through the microscopic tubules making up dentin, at a rate that activates mechanoreceptor nerves in the dentin pulp. When the surface of the tooth is eroded, the dentinal tubules become exposed to the external environment. The exposed dentinal tubules provide a pathway for transmission of fluid flow to the pulpal nerves and this is induced by changes in temperature, pressure and ionic gradients. By blocking the tubules, the external stimuli have a diminished effect, and less pain will be felt. A number of agents have been previously screened for their ability to occlude dentinal tubules, including potassium oxalate (Greenhill and Pashley, J Dent Res 60: 686-698, 1981).

Hypersensitive teeth can cause pain and discomfort when subjected to changes in temperature, pressure, or chemical action. Exposure of the dentin frequently leads to hypersensitivity. Dentin exposure may occur due to recession of the gums, periodontal disease and improper dental care.

Hypersensitive teeth are commonly treated with a nerve desensitizer such as potassium nitrate or potassium chloride. Alternatively, hypersensitive teeth may also be treated with an ingredient intended to occlude the tubuli, such as strontium acetate, strontium chloride, stannous fluoride, ferric oxalate or potassium oxalate. Application of the therapeutic ingredient may be via a non-prescription preparation, such as a dentifrice or rinse, or via products professionally applied or prescribed.

There have been various in vitro methods that have been developed to measure the effectiveness of various treatments and compositions to treat dentin so that it's less permeable. An effective method should reproduce the microenvironment in and around the tubule orifice, provide the correct geometry, appropriate surface chemistry, and relevant fluid composition and movement. One method was developed by Pashley (J. Periodontology, vol. 55, no. 9, pg. 522, September 1984). Pashley utilizes sectioned dentin discs of predetermined thickness which are placed between two o-rings within a two part chamber. Positive pressure is used to drive a testing fluid through the bottom chamber to the dentin section; the amount of fluid passing through the dentin is then measure to determine hydraulic conductance. The system was used to measure the effect of any desensitizing toothpastes had on reducing the permeability of the dentin.

One of the issues with the Pashley device has been with visualization. The upper portion of the device is usually covered so direct visualization of fluid moving through dentin is not possible. Further, as the dentin is covered by the top portion of the device in order to treat the dentin, for example by brushing with toothpaste or application of a tooth whitening strip) after a baseline measurement has been taken the top portion must be removed and then reattached, which could damage the dentin and/or alter the results.

Therefore, what is needed is a device allowing for direct manipulation of a dentin section while the dentin section is secured within the testing device, and which allows the dentin section to be visible during testing.

SUMMARY OF THE INVENTION

A method of visually recording the hydraulic conductance of a dentin section is provided that comprises preparing a dentin section; providing a test cell having a bottom component with an inner chamber; positioning at least a portion of the dentin section over the bottom component inner chamber; providing a fluid under pressure to the inner chamber of the bottom component; and visually recording hydraulic conductance of fluid through the dentin section.

A method of visually comparing the effect of oral care compositions on the hydraulic conductance of dentin sections is provided that comprises preparing a dentin section; providing a test cell having a bottom component with an inner chamber and a top component, wherein the top component comprises an opening having beveled walls; positioning at least a portion of the dentin section between the bottom component inner chamber and top component opening, providing a fluid under pressure to the inner chamber of the bottom component; visually recording hydraulic conductance of fluid through the untreated dentin section; treating at least a portion of the dentin section with an oral care composition; visually recording hydraulic conductance of fluid through the treated dentin section; and comparing the visually recorded hydraulic conductance of the treated and untreated dentin sections.

A method of visually comparing the effect of two or more oral care compositions on the hydraulic conductance of dentin sections is provided that comprises preparing a first dentin section; providing a test cell having a bottom component with an inner chamber and a top component, wherein the top component comprises an opening having beveled walls; positioning at least a portion of the first dentin section between the bottom component inner chamber and top component opening, providing a fluid under pressure to the inner chamber of the bottom component; treating at least a portion of the first dentin section with a first oral care composition; visually recording hydraulic conductance of fluid through the first dentin section; preparing a second dentin section; providing a test cell having a bottom component with an inner chamber and a top component, wherein the top component comprises an opening having beveled walls; positioning at least a portion of the second dentin section between the bottom component inner chamber and top component opening, providing a fluid under pressure to the inner chamber of the bottom component; treating at least a portion of the second dentin section with a second oral care composition; visually recording hydraulic conductance of fluid through the second dentin section; and comparing the visually recorded hydraulic conductance of the denting section treated with the first oral care composition and the second dentin section treated with the second oral care composition.

BRIEF DESCRIPTION OF THE DRAWINGS

FIG. 1 is a top view of a test cell bottom component for use in an embodiment of the present invention.

FIG. 2 is a sectional view of FIG. 1 along the 2-2 plane.

FIGS. 11A and 11B show pictures illustrating the hydraulic conductance of dentin sections according to an embodiment of the invention.

FIG. 12 shows pictures illustrating the hydraulic conductance of dentin sections according to an embodiment of the invention.

DETAILED DESCRIPTION OF THE INVENTION

Figure 3:
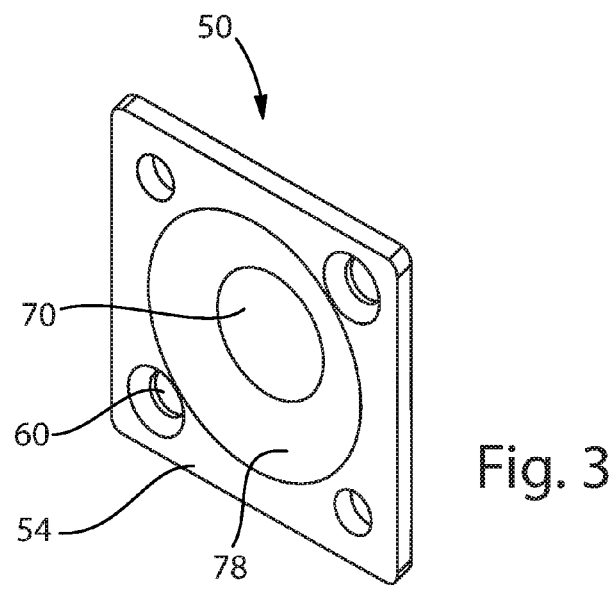
FIG. 3 is a perspective view of a test cell top component for use in an embodiment of the present invention.

Dental sensitivity is believed to be a result of rapid flow of fluid through dentinal tubulii caused by pressure changes, which are in turn a result of thermal or osmotic insults. The effectiveness of various oral care compositions at reducing sensitivity can be linked to their ability to block or reduce such fluid movement. As such, the methods of the present invention are designed to quantitatively compare, and visually record, the performance of oral care compositions and materials in blocking or inhibiting hydraulic conductance through dentinal tubulii.

All percentages and ratios used hereinafter are by weight of total composition, unless otherwise indicated. All percentages, ratios, and levels of ingredients referred to herein are based on the actual amount of the ingredient, and do not include solvents, fillers, or other materials with which the ingredient may be combined as a commercially available product, unless otherwise indicated.

All measurements referred to herein are made at 25° C. unless otherwise specified.

By "oral care composition", as used herein, is meant a composition, which in the ordinary course of usage, is not intentionally swallowed for purposes of systemic administration of particular therapeutic agents, but is rather retained in the oral cavity for a time sufficient to contact dental surfaces or oral tissues. Examples of oral care compositions include dentifrice; mouth rinse; mousse; foam, mouth spray; lozenge; chewable tablet; chewing gum; dental strips, such as tooth whitening strips, sensitivity strips, or breath freshening dissolvable strips; floss and floss coatings; or denture care or denture adhesive product. The oral care composition may also be incorporated onto strips or films for direct application or attachment to oral surfaces.

The term "dentifrice", as used herein, includes tooth or subgingival-paste, gel, or liquid formulations unless otherwise specified. The dentifrice composition may be a single phase composition or may be a combination of two or more separate dentifrice compositions. The dentifrice composition may be in any desired form, such as deep striped, surface striped, multilayered, having a gel surrounding a paste, or any combination thereof. Each dentifrice composition in a dentifrice comprising two or more separate dentifrice compositions may be contained in a physically separated compartment of a dispenser and dispensed side-by-side.

The term "dispenser", as used herein, means any pump, tube, or container suitable for dispensing compositions such as dentifrices.

The term "teeth", as used herein, refers to natural teeth as well as artificial teeth or dental prosthesis.

The term "visually recorded", as used herein refers to visual observation of the appearance and rate of appearance of liquid. Using a camera or other visual recordation device, this may be performed in real time or captured via still or video photography for incorporation and replay in hardcopy or digital media; may also include quantitative analysis of the size of liquid droplets or area occupied by liquid droplets.

The term "hydraulic conductance", as used herein refers to convective liquid movement, specifically pressure driven movement of liquid. Mathematically it is described by the volumetric flow rate (Q) divided by the area of the flow window (A) and the pressure drop across the thickness of the dentin section (ΔP) as shown below and as described in the literature (see J Dent Res 1981, 60(3):pp 686-698 for an example)

$$L_p = \frac{Q}{A(\Delta P)}$$

Where $L_p$ is hydraulic conductance, (A) is the defined area of liquid flow, and (ΔP) is the pressure drop across the thickness of the dentin section, and (Q) is volumetric flow rate.

In the present invention hydraulic conductance rates are measured through a cross-section of dentin to evaluate and visually record the effect of treatment with an oral care composition. Examples of treatment include application via toothbrush, oral rinse, dental strip or patch, swab applicator, manually rubbing with a finger, and application via burnishing tool such as a prophy cup. The method may comprise one or more of the following steps: dentin section preparation, mounting the section in a test cell, measurement and visual recording of baseline hydraulic conductance under pressure, treatment with one or more oral care compositions, and measurement and visually recording of hydraulic conductance post treatment. A comparison is then made of the visually recorded results between treated and untreated and/or different treatments. Results may also be reported in terms of percentage reduction in rate.

Dentin Section Preparation

Dentin sections of human molars can be obtained in as close proximity to the enamel junction as possible without residual enamel appearing on the surface of the cross-section. Sections may be cut and sanded to a thickness of between about 0.1 mm to about 2 mm, however sections are typically cut and sanded to a thickness between about 0.8 mm to about 1 mm, although larger or smaller specimens may be used. Thicker sections are typically marred by residual enamel on one surface or the appearance of pulpal horns on the other. Section thickness down to about 0.1 mm may be used, but sections thinner than about 0.4 mm can be very fragile and more difficult to work with. In certain embodiments, a constant section thickness is used for multiple samples, for example about 0.8 mm, so that the pressure drop per unit thickness remains consistent from sample to sample. To remove the smear layer resulting from the cutting/sectioning/sanding process, samples may be sonicated in de-ionized (DI) water for a period of time, such as about 6 minutes on each side, followed by acid-etching in an ultrasonic bath operated at 15 kz, such as the Bronson Model 1510 Ultrasonic Cleaner (Fischer Scientific, Pittsburgh, Pa.) in 10 ml of 6.0% citric acid for a certain amount of time, such as about 2 minutes on each side to remove the smear layer deposited by cutting and sanding. Samples may then be rinsed with DI water followed by immersion in commercial phosphate-based pH 7 calibration buffer containing a microbial growth inhibitor, such as BDH pH 7 Reference Standard Buffer (VWR p/n BDH5052, Radnor, Pa.). Water may be used as a short-term storage solution, but refrigeration in a dilute thymol solution may be used for long-term storage.

FIGS. 1 through 6 are views of a test cell 10 that may be used in the present invention. FIG. 1 is a top view of the bottom component 20 of test cell 10, while FIG. 2 is a vertical sectional view of FIG. 1 along the 2-2 plane. Bottom component 20 of the test cell includes bottom surface 22, top surface 24, indent 26, inner chamber 30, fastener blind holes 32 (or other suitable mechanism for engaging fasteners), inlet channel 34, and flush channel 36. In certain embodiments, inlet channel 34 and flush channel 36 may be positioned opposite or substantially opposite each other. Inlet channel 34 and flush channel 36 each have an inner end, 34a and 36a, respectively, the inner openings, 34a and 36a, joining inlet channel 34 and flush channel 36 to the inner chamber 30. The inner openings, 34a and 36a, further define the point from which inlet channel 34 and flush channel 36 extend outwardly from the test cell 10.

The bottom component 20 comprises an opening 40 at the top of the inner chamber 30 for accessing the inner chamber 30. Inlet channel 34 is positioned in fluid communication with inner chamber 30. Flush channel 36 is also positioned in fluid communication with inner chamber 30. Inlet channel 34 and flush channel 36 can be, optionally, as shown in FIG. 7, threaded to receive the compatibly threaded ends of inlet and flush tubes 110 and 112, respectively.

Figure 4:
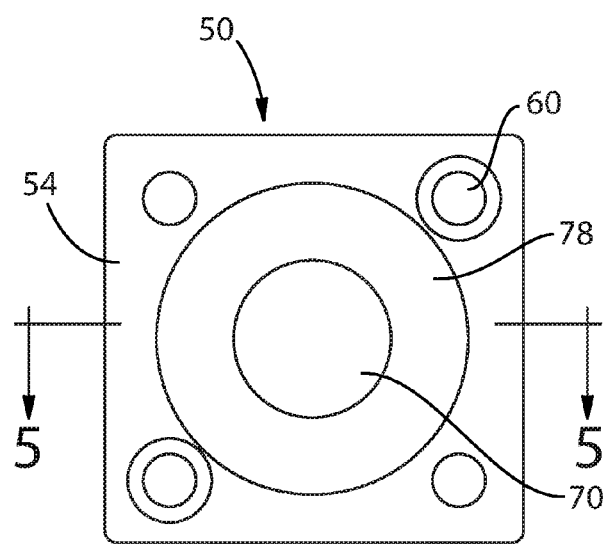
FIG. 4 is a top view of a test cell top component for use in an embodiment of the present invention.
Figure 5:
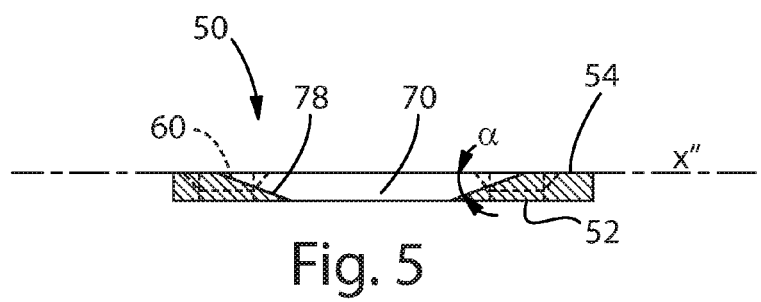
FIG. 5 is a sectional view of FIG. 4 along the 5-5 plane.

FIG. 3 is a perspective view of the top component 50 for test cell 10; FIG. 4 is a top view of the top component 50 for test cell 10; while FIG. 5 is a vertical sectional view of FIG. 4 along the 5-5 plane. The top component 50 of the test cell includes bottom surface 52, upper surface 54, optional fastener through-holes 60 (or other suitable mechanism for engaging fasteners), and top component opening 70. Top component opening 70 is defined by walls 78 on top component 50. The walls 78 may be beveled towards the top component opening 70 at an angle "a" as determined by the XY plane, having its vertex at the intersection of the wall 78 and upper surface 54 of the top component, wherein the angle α can be from about 30° to 85° or from about 50° to about 75°. The beveled walls 78 allow easy access to oral care compositions and devices to apply oral care compositions, which can be used to treat the dentin, such as whitening strips and toothbrushes.

Figure 6:
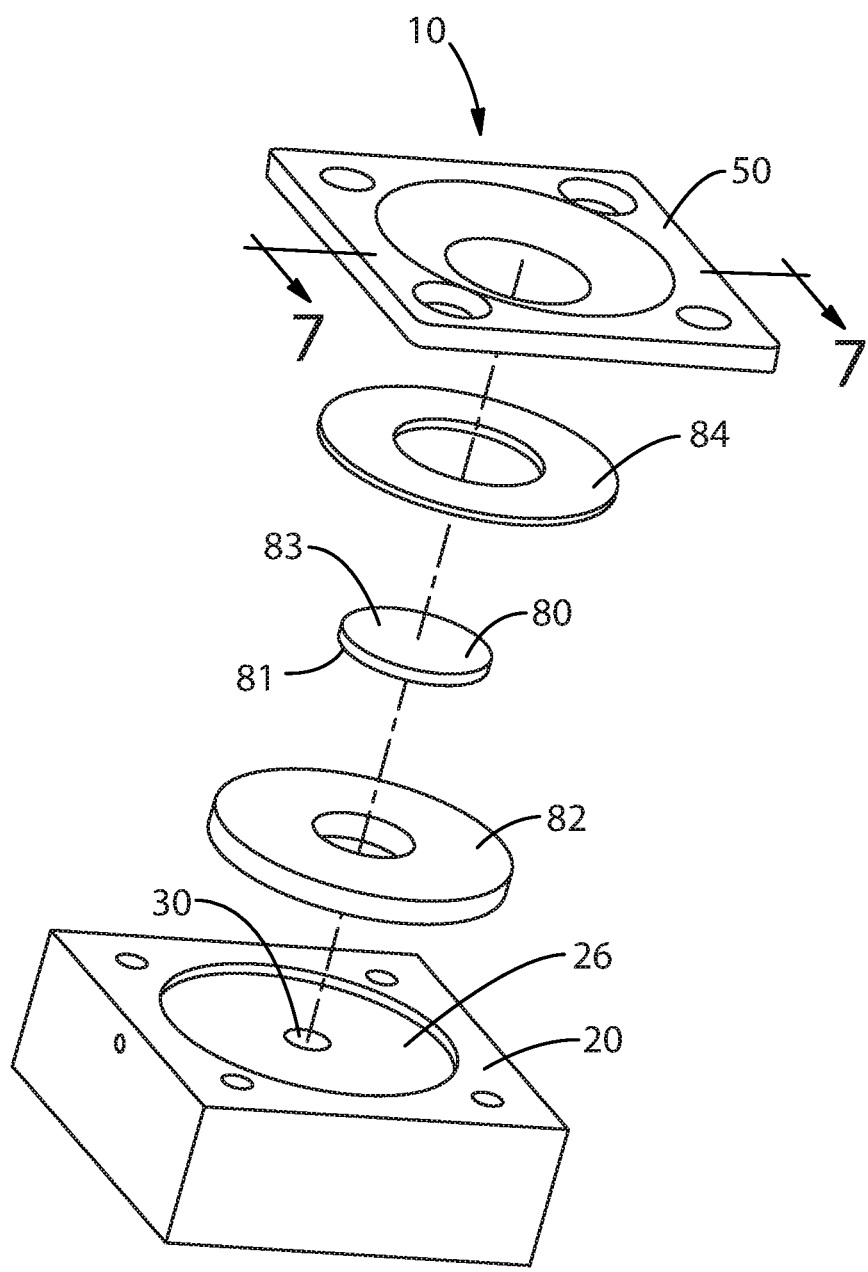
FIG. 6 is an exploded view of a test cell for use in an embodiment of the present invention.
Figure 7:
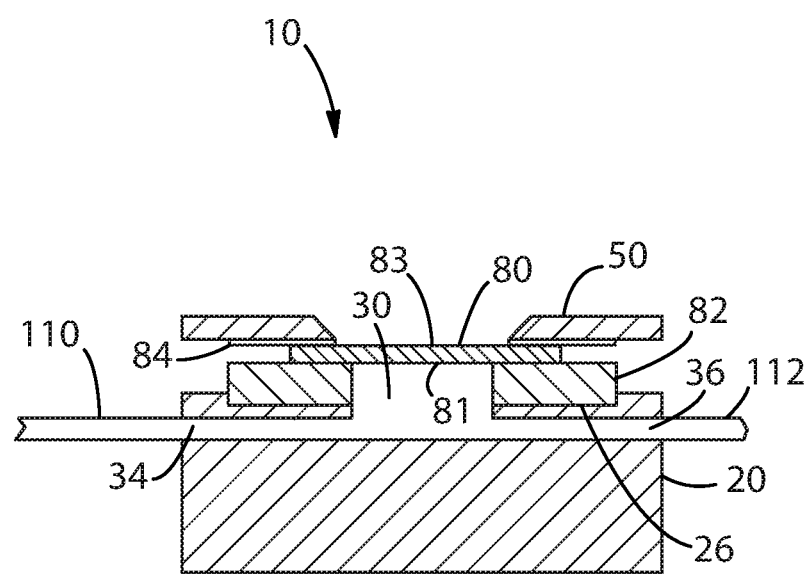
FIG. 7 is a sectional view of FIG. 6 in an assembled state along the 7-7 plane.

As shown in FIGS. 6 and 7, in certain embodiments, top component 50 and bottom component 20 are shaped to fit one in the other so as to permit a secure engagement between the two components, to form a test cell 10. FIG. 7 is a cross-sectional view of the test cell shown in FIG. 6, in an assembled state, with inlet and flush tubes 110 and 112 connected with inlet channel 34 and flush channel 36, respectively. The top component 50 and bottom component 20 components may be formed from machined glasses; woods; metals, such as stainless steel; plastics, such as polymethyl methacrylate (PMMA) or polycarbonate (PC); or a combination of these materials. In one embodiment, top component 50 and/or bottom component 20 are formed from (e.g., by machining) optically clear or transparent PMMA, such as that available from MacMaster-Carr (Catalogue #8560K912 or #8560K265) of Robbinsville, N.J. The advantage of using a clear (e.g., optically clear or transparent) material in forming test cell 10 is that clear materials allow "line of sight" into the cell or otherwise makes the contents of the cell visible to the unaided eye to, for example, help in visually determining whether all air in the form of air bubble(s) has been purged from the portion of inner chamber 30 below the dentin section 80. An air bubble below the dentin section 80 decreases the area of dentin section 80 through which fluid can flow through, which may result in an inconsistent measurement of permeability through the dentin.

As shown in FIGS. 6 and 7 the test cell may be assembled by placing first washer 82 in indent 26 of bottom component 20. Second washer 84 is positioned under top component 50. In certain embodiments, indent 26 of bottom component 20 is machined to fit the width dimensions of any washer(s) used (such as washer 82) so as to reduce, minimize or prevent any displacement of the washer(s): i) as the components of the test cell are being secured for use (e.g., testing and/or fluid hydraulic conductance measurement); and/or ii) during actual use (e.g., testing and/or fluid hydraulic conductance measurement). Second side 81 of dentin section 80 is placed on first washer 82. The dentin section 80 is centered over the opening in the first washer 82 with the enamel side (first side 83) corresponding to the occlusal surface of the tooth facing up, i.e. facing the second washer 84 and top component 50, making sure that the section 80 either completely spans the opening or sufficiently contacts enough of the perimeter such that the section 80 is held securely in place. Washer 84 is placed on first side 83 of dentin section 80. To complete sealing of the cell, top component 50 is fastened onto bottom component 20, using fasteners, for example the fasteners may be screws which pass through optional fastener through-holes 60 of top component 50 and are anchored in/by fastener blind holes 32 of bottom component 20 having screw holes suitable for engaging the screws so that the screws adjustably tighten and seal the top component 50 on to bottom component 20. In this embodiment the test cell, including top component 50 and bottom component 20 is referred to as test cell 10. Fasteners may be formed of materials such as stainless steel.

Alternatively, the assembly of top component 50 on to bottom component 20 can be accomplished by the use of other adjustable fastening mechanisms, such as nails, dowels, clamps, straps, bolts (e.g., screw-type), or any other fastening mechanism suitable for providing a leak proof (or substantially leak proof) seal and allow for ready disassembly and assembly. Optionally, the fastening mechanism can operate by friction or interference fit so long as the friction or interference fit can withstand the fluid pressures used in the present invention.

The test cell 10 used in the present invention differs from "Pashley" type flow-through cells reported in the external literature in that it includes a top component 50, which allows sealing the dentin section 80 in the test cell while maintaining access to one of the dentin section 80 surfaces. The area defined by the first washer 82 underneath the dentin section 80 remains constant throughout the conditioning, baseline measurement, and post-treatment hydraulic conductance measurement. This is a significant advantage in comparison to devices which require disassembly between baseline and post-treatment measurements in order to apply a treatment to the dentin section surface, because quantitative hydraulic conductance is a strong function of the specific hydraulic conductance window selected. Our experience has shown that quantitative precision is improved when the same hydraulic conductance window is utilized to compare pre- and post-treatment measurements to show hydraulic conductance reduction. A second advantage to having a top component 50, as used in the present invention is the unobstructed view of the dentin section surface. After excess moisture has been removed, still or video photography may be used to visually record images of liquid droplets coalescing on the dentin section surface.

Figure 8A:
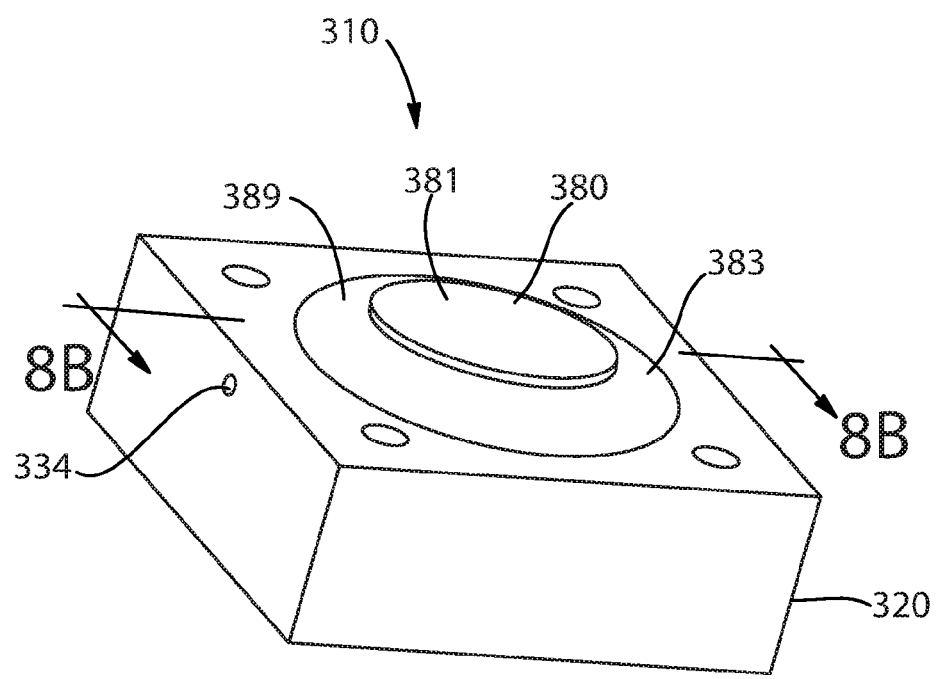
FIG. 8A is a perspective view of a test cell for use in an embodiment of the present invention.
Figure 8B:
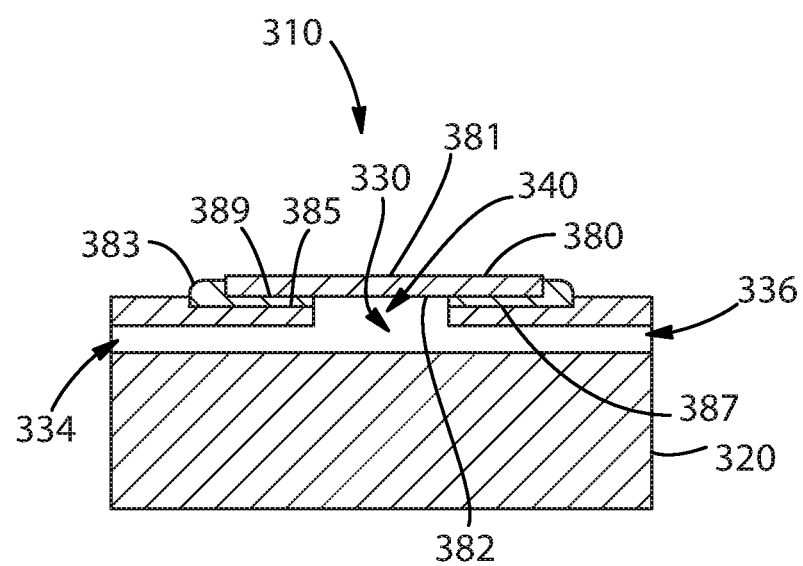
FIG. 8B is a sectional view of FIG. 8A along the 8B-8B plane.

In certain embodiments of the present invention, as illustrated in FIGS. 8A and 8B, a test cell 310 may be used that does not include a top component. The assembled test cell 310 comprises a bottom component 320 having an opening 340 at the top of an inner chamber 330 for accessing the inner chamber 330. Inlet channel 334 is positioned in fluid communication with inner chamber 330. Flush channel 336 is also positioned in fluid communication with inner chamber 330. In this embodiment the test cell 310 also comprises a washer 383 and a dentin section 380. Second side 382 of dentin section 380 faces the washer 383. The dentin section 380 is centered over the opening in the washer 383 with the enamel side (first side 381) corresponding to the occlusal surface of the tooth facing up, making sure that the dentin section 380 either completely spans the opening or sufficiently contacts enough of the opening perimeter such that the section 380 is held securely in place. The washer 383 forms a liquid-tight seal between the bottom component 320 and the dentin section 380 establishing fluid communication between the bottom component 320 and dentin section 380. The water tight seal can be produced by a free-standing adhesive substance, or by a combination of a self-adhesive washer in combination with a waterproof adhesive substance present on the washer first surface 387 (faces the bottom component) and the washer second surface 389 (faces the dentin section). In certain embodiments the second surface 389 may include a notch 385, so that a dentin section 380 may rest, at least partially, within the washer 383. In this embodiment adhesive would be present within the notch. An example of a suitable adhesive substance includes silicone-based bonding agents such as Dow Corning Number 700 Silicone Sealant (McMaster-Carr p/n 7425A51). An example of a suitable material from which washers may be cut is Buna-N rubber (McMaster-Carr p/n 86795K21). After cleaning with liquid dishwashing detergent, the washer may be coated on both sides with the adhesive substance or may be clamped or pressed in place until the sticky material forms a water-tight seal between the dentin and bottom component.

The "washers" that may be used in the present invention may have at least one flat side for contacting a dentin section, bottom component, or top component. Washers may be made of, silicon, rubber or soft plastic. Examples of such silicon, rubber or soft plastic materials, include, but are not limited to, butadiene rubber, butyl rubber, chlorosulfonated polyethylene, epichlorohydrin rubber, ethylene propylene diene monomer, ethylene propylene rubber, fluoroelastomer, nitrile rubber, perfluoroelastomer, polyacrylate rubber, polychloroprene, polyisoprene, polysulfide rubber, sanifluor, silicone rubber and styrene butadiene rubber) and thermoplastics (including, but not limited to, thermoplastic elastomer; thermoplastic polyolefin, thermoplastic polyurethane, thermoplastic etheresterelastomers, thermoplastic polyamide(s), melt processible rubber thermoplastic vulcanizate) and mixtures thereof. In one embodiment, the washers may be rubber "O"-rings supplied by McMaster-Carr (Catalogue #4061T114) of Robbinsville, N.J.

The permeability of dentin section 80 may be measured using test cell 10 in the present invention in the following manner. Once the two-part test cell 10 is assembled, pressure is used to initiate and maintain fluid (e.g., distilled water) flow in inlet channel 34. In the embodiment shown in FIG. 7, fluid flows into the bottom component 20 through inlet channel 34, and into the portion of inner chamber 30 below dentin section 80. Initially, flush channel 36 is kept open so that residual air in the form of air bubble(s) located in the portion of inner chamber 30 below dentin section 80 flows into flush channel 36 and exits test cell 10. When the residual air has been removed, flush channel 36 is closed. When flush channel 36 is closed, fluid pressure rises in the portion of inner chamber 30 below dentin section 80. This increased fluid pressure initiates fluid hydraulic conductance in (across or through) the dentin tubule orifices in dentin section 80. Fluid hydraulic conductance continues through top component opening 70 of top component 50.

Figure 9:
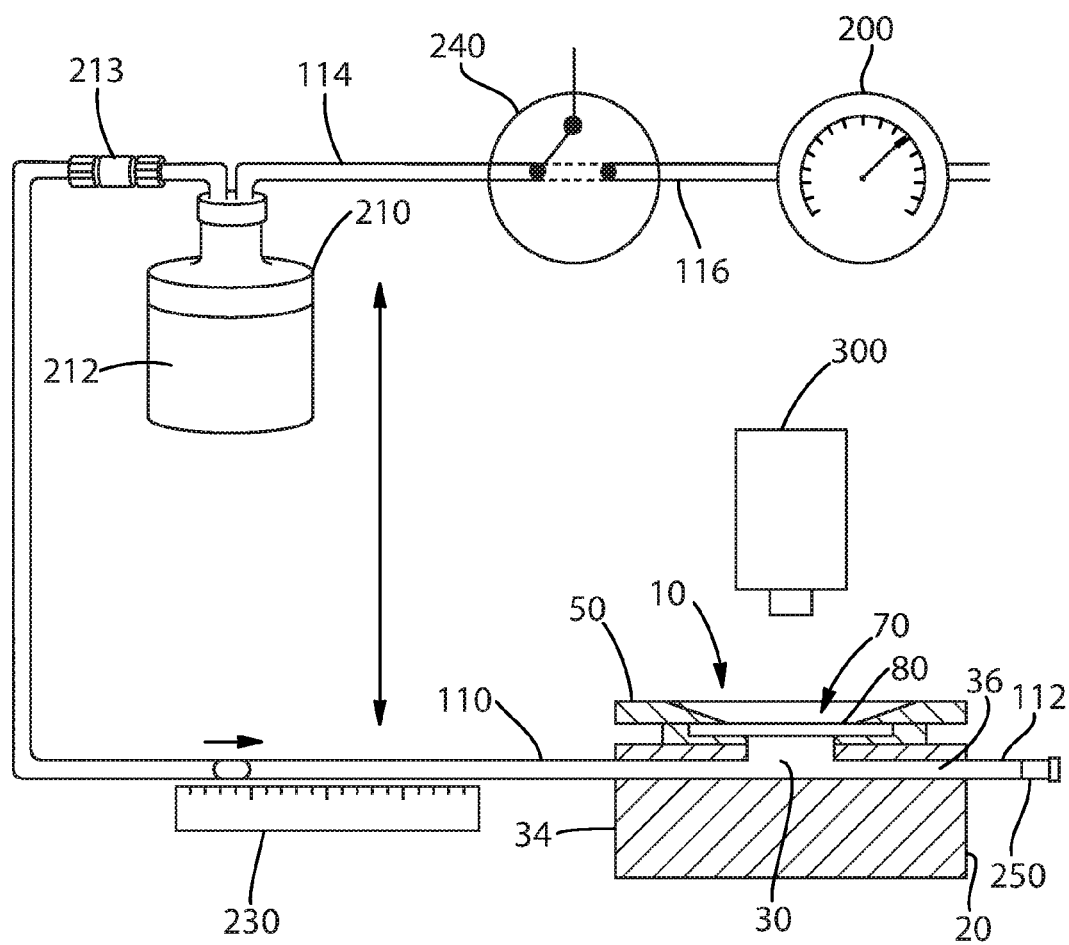
FIG. 9 is a schematic drawing of a system layout for visually recording dentin permeability according to an embodiment of the present invention.

FIG. 9 is a schematic flow chart drawing, explaining the equipment lay-out for use in the method of measuring the permeability of dentin according to an embodiment of the present invention. Though this is one possible lay-out of for the equipment, it is to be understood that other possible lay-outs would also be useful in the method of measuring the permeability of dentin according to the present invention.

The schematic flow chart drawing includes, in fluid communication: pressure generating device 200; fluid source 210; flow meter 230; tubes 110, 112, 114, and 116; and valve 240. Tube 116 connects pressure generating device 200 to valve 240. Tubes 110, 112, 114, and 116, may be metal or plastic. In one embodiment, the tubes are as $\frac{1}{16}"\times\frac{1}{32}"$ Tefzel or PTFE Tubing (Idex Corp., Lake Forest, Ill.). The flow chart also includes a camera 300 for visually recording hydraulic conductance of dentin samples.

Fluid source 210 could be plastic, metal or glass. For example, fluid source 210 could be a one-liter media bottle supplied by Kimble Chase Life Science and Research Products LLC, Vineland, N.J., with a GL-45 Q-type Bottle cap 3 way ¼-28 fitting ports (Fisher Scientific #00945Q-3). Fluid 212 may be water, distilled water, or de-ionized water (DI). In certain embodiments, Fluid 212 may consist of a mixture of proteins and salts, which to varying degrees, may approximate physiological pulpal fluid. Examples of simulated pulpal fluid include whole bovine plasma such as Sigma-Aldrich product P4639, Hartmanns solution, Lactated Ringers solution (Sigma-Aldrich, St. Louis, Mo.), or protein-containing simulated pulpal solution, described below. A visible dye, such as FD&C Blue #1 (cas #3844-45-9) or fluorescent dye, such as Rhodamin B (cas#81-88-9), may also be used to improve contrast between fluid and dentin or otherwise enhance the visual effect of fluid appearance and movement.

Pressure generating devices, include pumping mechanisms (or sources of pressure) such as, static fluid pressure, piston pumps, rotary piston pumps, diaphragm pumps, gear pumps, or double-action piston pumps.

Pressurized inert gas flows from pressure generating device 200 through valve 240, and into the headspace above fluid 212 in fluid source 210. Tube 114 and valve 240 are in fluid communication with fluid source 210, and are used for venting fluid source 210, if necessary.

The pressurization of fluid source 210 causes fluid 212 to exit fluid source 210 through fittings 213 on the union adjacent to the fluid source 210 and inlet tube 110. The fittings may comprise any combination of fasteners which allow a reversible interruption of a secure liquid seal, such as a threaded Upchurch plastic bolt/union combination (IDEX Corp. p/n P-760, Lake Forest, Ill.). In certain embodiments, in addition to the pressure exerted on the fluid 212 by the pressure generating device 200, the fluid source 210 can be positioned above the test cell 10 (represented by up and down arrow in FIG. 9); for example the difference in height between the fluid source 210 and test cell 10 may be between about 5 cm to about 100 cm or from about 15 cm to about 70 cm. The difference in height can be used to exert controlled fluid pressure, which in turn induces liquid flow through dentinal tubules during treatment phase. The liquid flow is important in order to mimic natural physiological conditions in the tubuli which exist during treatment, including indigenous mineral transport and resistance to diffusive penetration of therapeutic agents. The fluid in inlet tube 110 passes through flow meter 230, and enters test cell 10 through flow inlet channel 34. A bubble for measuring the flow rate may be introduced to the inlet tubing 110 just downstream from the fluid source 210 by releasing the pressure via disconnecting the fittings 213 on the union adjacent to the fluid source 210, and raising the inlet tubing 110 above the fluid source 210 until a bubble is visible. Flush tube 112 is connected to and, as earlier noted, in fluid communication with flush channel 36 of test cell 10. Effluent valve 250 is located on flush tube 112 to bleed residual air (or, air bubbles) located in the portion of inner chamber 30 below dentin section 80 at the start of a dentin permeability measurement. Fluid exits test cell 10 via through top component opening 70 of top component 50.

In certain embodiments, the flow rate meter 230 is a high precision flow meter. When used to describe the flow rate meter, the phrase "high precision" means a flow meter having an instrument resolution of below about 0.5 microliter per minute, or optionally below about 0.5 nanoliters. The flow meter can be a manual or digital flow meter. Flow meter 230 acts as a measuring device suitable for measuring and/or determining hydraulic conductance through dentin section 80. In certain embodiments, the flow rate meter is calibrated to measure fluid flow rates of from about 0 to about 400 microliter per minute, optionally from about 0 to about 200 microliter per minute, or optionally from about 0 to about 150 microliter per minute. Examples of manual flow rate meters that can be used include those supplied by Gilmont Instruments (Barrington, Ill.), including the direct reading flowmeter Gilmont Flowmeter GF2000 and the correlated flowmeter Gilmont Flowmeter GF3000. Examples of digital flow rate meters that can be used include the Sensirion SLG1430-025 flowmeter supplied by The Sensirion Co. (Westlake Village, Calif.) and such flow meters supplied by Bronkhorst High-Tech (Bethlehem, Pa.) as the thermal liquid mass flowmeter Micro-FLOW series L01 Digital Mass Flow Meter. In some embodiments, a second flow rate meter may be used with flow rate meter 230 to confirm that the fluid flow rate in the system of the present invention falls within the range that flow rate meter 230 is calibrated to measure (as described above). In other embodiments, one flow rate meter (manual) could be used to verify the more accurate reading of a second, digital flow rate meter. Tubes 110, 112, 114, and 116, may be metal or plastic. In one embodiment, the tubes are Tube Tefzel (Natural 1/16*0.040*50 ft), available from Upchurch—IDEX health and Science, Bristol, Conn.

After preparation and mounting, each dentin section may undergo a sequence involving (1) formation of pellicle→(2) conditioning→(3) baseline hydraulic conductance measurement→(4) treatment→(5) post-treatment hydraulic conductance measurement. Steps (4) & (5) may be repeated. In some cases, the method of the present invention may conclude with an acid challenge and final hydraulic conductance measurement step.

Pellicle Formation

In some cases, formation of a biological pellicle along the surface of the dentin and inner tubuli surfaces may be desired to more closely mimic physiological systems. To form a pellicle, mount a dentin section in a test cell, as shown in FIGS. 6 and 7, and pass filtered saliva or other protein-containing mimic of pulpal fluid through inlet tubing 110 and exiting outlet tubing 112 to flush air bubbles from liquid chamber 30 of the bottom component 20 prior to stopping outlet tubing 112 and application of fluid pressure to force protein-containing fluid through the dentin section to contact all tubuli surfaces. Deposition of a robust pellicle may require prolonged contact between solution and dentin of about 0.5 to about 12 hours or more.

Conditioning

In certain embodiments the dentin section may be conditioned, wherein an oral care composition is used to directly treat a portion of the dentin section, for example by brushing the enamel surface with a sonic powerbrush (e.g. Oral B Triumph Professional Care, The Procter & Gamble Co., Cincinnati, Ohio). To produce accurate flow reduction measurements a stable background flow is often used. Otherwise, it is difficult to ascertain how much of the change in flow is a result of treatment vs. background flow variation, which is an inherent problem in working with dentin. We've found empirically that vigorously brushing the dentin surface has the effect of stabilizing background hydraulic conductance. For example, it may be difficult to get repeat measurements of hydraulic conductance to stabilize within 5% unless this conditioning procedure is followed. Further, lightly brushing at a defined period of time before each flow measurement is made improves reproducibility and consistency. For example, lightly brushing with a dampened manual toothbrush (ADA standard reference toothbrush from Ranir Corp p/n 101044100, Grand Rapids, Mich. or CVS Pharmacy p/n 29470A) for 30 seconds just prior to each evaluation of flow measurement may limit the amount of drift in background flow and enable a more reproducible evaluation of hydraulic conductance.

Baseline Hydraulic Conductance Measurement

To establish a reference point for the % flow reduction measurement, flow rate of a fluid 212 can be measured by visually monitoring progress of an air bubble adjacent to a ruler, atop a light box, as discussed previously.

Treatment

A dentin section or portion thereof may be treated using one or more oral care compositions, for example by using a dentifrice. A quantity of dentifrice can be dispensed to an ADA standard reference toothbrush, which is then used to apply the dentifrice to the dentin section. Following application the oral care composition is then rinsed, for example by using a laboratory wash bottle, direct a stream of DI water or other fluid with composition similar to fluid 212 around the dentin section to rinse away residual oral care composition.

In certain embodiments a dentin section may be treated with a coated whitening strip. For treatment a section of the whitening strip is removed, such as by using a circular tool (ex. arch punch), to punch out a coated whitening strip disk having a smaller diameter than the top component opening 70. Treat for a timed period, remove the whitening strip disk, and rinse the dentin section with water.

Post-Treatment Hydraulic Conductance Measurement

As described previously under "Baseline Flow Measurement," hydraulic conductance comparative results can be expressed as % reduction in hydraulic conductance as per the equation shown below:

$$\% \text{ Reduction} = 100 \frac{(Q_p - Q_b)}{Q_b}$$

Where $Q_p$=post-treatment hydraulic conductance, and $Q_b$=baseline hydraulic conductance.

Hydraulic conductance may also be visually recorded by placing a suitable camera or recorder, preferably one having a zoom or magnification capability of at least about 100× and video capability of at least about 30 frames per second, such as the EVOS-XL digital camera (Electron Microscopy Sciences p/n 6500-XL, Hatfield, Pa.), or Pro-Scope HR2 (Electron Microscopy Sicences p/n 68350-65-2), or USB Digital Microscope (Trait Technology Co. Limited, Shenzhen, PRC, p/n T-Microscope-1011) above the mounted dentin section prior to application of pressure to the fluid source. Still photographs and video sequences can be acquired pre- and post-treatment to aid in communicating concepts associated with liquid hydraulic conductance and reduction in hydraulic conductance. Multiple cameras may be utilized at various angles and various times to capture additional visual perspectives. One example of the many suitable photographic configurations involves a USB camera, such as the Pro-Scope HR2, mounted directly above and at right angles to the surface of the dentin section, utilizing lighting directed from the camera or from the same angle as the camera, capturing still images or video at 30 frames per second for up to about 10 minutes, for example for about 10 seconds, 30 seconds, one minute, or five minutes. Magnification and camera proximity, as illustrated in FIG. 9, may be chosen such that the observation frame includes the entire dentin section 80 visible through the opening 70 of top component 50, as well as the edges of the top component 50 surrounding the opening 70. The dentin section surface is typically wiped dry with a laboratory tissue or lint-free cloth prior to focusing and optimizing image contrast. Image or video acquisition is typically initiated at or just prior to application of liquid pressure, which in turn causes liquid flow through the dentin section and the appearance of liquid on the surface of the dentin section. Liquid pressures from about 0.5 psi to about 100 psi, about 5 psi to about 90 psi, about 10 psi to about 70 psi, or about 20 psi to about 50 psi, may be consistent with pain-inducing conditions described in the literature (see D. H. Pashley et. al., "Dental Pain Evoked by Hydrostatic Pressures Applied to Exposed Dentin in Man: A Test of the Hydrodynamic Theory of Dentin Sensitivity", Journal of Endodontics, Vol 20(3), 1994, pp. 130-134). In certain embodiments, a reduced pressure of about 1 to about 10 psi applied across about a 0.8 to about a 1.0 mm section of the dentin may extend the time-frame of liquid appearance, such that the viewer has sufficient time to understand and comprehend the phenomenon.

EXAMPLES

The following procedure was used to prepare the test cell and dentin sections for testing.

Preparation of Cell Components

Inlet and flush tubes were fitted to the inlet and flush channels of test cell bottom component by fitting tubing (1/16"×1/32" Tefzel or PTFE Tubing; Idex Corp., Lake Forest, Ill.) through the channel. This was accomplished by forcibly drawing out the tubing to expose a narrowed section, cutting the tubing at approximately the location where the outer diameter is smallest, inserting the narrowed end within the desired channel (inlet or flush), grasping the protruding end, pulling about 3-4 inches of tubing through the hole, and trimming the protruding end. Test cell components, including washers, were washed with an SLS-based detergent and thoroughly rinsed.

Mounting Dentin Sections

Dentin sections were centered over the opening of flat first washers (1/16" buna-N material) with the occusal side up, i.e. facing the top component, making sure that the dentin section spans the opening with at least 1 mm overlap at each location around the perimeter. To allow for a dentin section treatment protocol involving brushing and/or application of a strip or smear-layer, the test cell was assembled with a second washer (also 1/16" buna-N material) and the top component.

To form a pellicle the fluid source was filled with Hartmanns solution. Hartmanns solution was prepared by combining the following with approximately 1.8 liters of DI water in a 2 L volumetric flask at room temperature, and then mixing until the salts were visibly dissolved:

6.8 g Lactic acid
0.59 g $CaCl_2$
0.75 g KCl
11.7 g NaCl

A sufficient quantity of 50% NaOH (1-2 mL) was then added drop-wise to bring the solution to pH 7 before bringing the flask to volume with additional DI water.

Once filled with Hartmanns solution, 30 psi of pressure was applied to the fluid source, via regulated laboratory gas service, and the effluent valve on the flush tube opened to momentarily (1 to 3 seconds) flush the inner chamber and pulpal side of the dentin section. The effluent valve was then closed, pressure released from the fluid source, and the Hartmann's solution replaced with simulated pulpal fluid. Simulated pulpal fluid (SPF) was prepared by addition of 1.2 g of Bovine Serum Albumin, such as p/n A2153 from Sigma-Aldrich, to a sufficient volume of Hartmanns solution, with mixing, to obtain a visually homogeneous solution volume of 100 mL. Simulated pulpal solution was allowed to flow through the dentin section under 30 psi pressure for 15 minutes to ensure contact with all dentin surfaces.

The pressure was reduced by means of valve 240, allowing the SPF to flow under a modest head pressure produced by elevation of the fluid source by 30 cm for 1 hour. During this time, 200 µl of pooled human saliva was pipetted and allowed to sit directly atop the dentin section.

At the end of the one hour period, the saliva was rinsed with an indirect stream of room-temperature Hartmanns solution using a washbottle. The SPF was replaced with Hartmann's and the inner chamber flushed for several seconds with Hartmanns solution under a pressure of 30 psi.

In preparation for measurement of baseline hydraulic conductance, the dentin section was conditioned by brushing the enamel surface with a sonic powerbrush (e.g. Oral B Triumph Professional Care, The Procter & Gamble Co. Cincinnati, Ohio) for two minutes, pausing to rotate the dentin section every thirty seconds, initially and periodically wetting the brush with Hartmanns solution. During the conditioning procedure and for 5 minutes thereafter, Hartmanns solution was continually forced through the dentin under 30 psi of pressure. After measurement of hydraulic conductance (see hydraulic conductance measurement), the sample was subjected to a mechanical challenge by brushing the dentin surface with a conventional (manual) toothbrush such as an ADA standard reference toothbrush (Ranir Corp p/n 101044100, Grand Rapids, Mich. or CVS Pharmacy p/n 29470A), wetted with Hartmanns solution, for 2 minutes before obtaining a second hydraulic conductance measurement. If necessary, the conditioning procedure was repeated until hydraulic conductance measurements before and after the mechanical challenge varied by less than 7%. This was done to demonstrate a stable baseline hydraulic conductance, enabling meaningful comparison of hydraulic conductance before and after treatment, even when the treatment involved direct contact with the dentin, e.g. tooth brushing.

Quantitative Hydraulic Conductance Measurement

The hydraulic conductance of Hartmanns solution through the dentin section was measured prior to and following one or more therapeutic treatments by visually monitoring progress of an air bubble adjacent to a ruler, atop a light box. The bubble was introduced to the inlet tubing just downstream from the fluid source by releasing the pressure via the valve in FIG. 8, disconnecting the fitting (IDEX corp p/n P-760) on the union adjacent to the fluid source, and elevating the inlet tubing above the fluid source until about a 2 inch to about 5 inch bubble was visible. The fluid source fitting was retightened, 30 psi pressure reapplied and hydraulic conductance measured. At least four time vs. linear distance data points were obtained by visually monitoring progress of an air bubble adjacent to the ruler atop a light box and periodically recording bubble position vs. elapsed time as measured by stopwatch. Bubble translation was converted to volume by multiplying by the appropriate conversion factor, e.g. 12.6 ul/in for 1/32 ID tubing. Using linear regression, i.e. the SLOPE function in Microsoft excel software, the hydraulic conductance rate was calculated from the slope of time vs. volume data.

Separately, video photography of fluid movement was also obtained prior to and following one or more therapeutic treatments with a digital microscope (USB Digital Microscope, p/n T-Microscope-1011, Trait Technology Co. Limited, Shenzhen, PRC). The microscope was placed directly above and at right angles to the surface of the dentin section, utilizing lighting directed from the LED bulbs surrounding the camera lens. Magnification (approximately 100×) and camera proximity were chosen such that the entire dentin section exposed through the opening of the top component of the test cell, including edges of the top component surrounding the opening were within the observation frame. The dentin surface was wiped dry with a laboratory tissue prior to focusing the camera, after which lighting, image hue, and contrast were optimized to give an accurate and sharp image. Video acquisition was typically initiated at 15 frames per second just prior to application of 5 pounds per square inch (psi) of liquid pressure, and concluded between 8 and 20 seconds after application of liquid pressure. VirtualDub software (Avery Lee, v. 1.9.11) and Camtasia Studio software (TechSmith Corp, ver 7.1.0, Okemos, Mich.) were used to crop and overlay video tracks, respectively, to enable side-by-side comparisons.

Example 1: Whitening Strip

Figure 10:
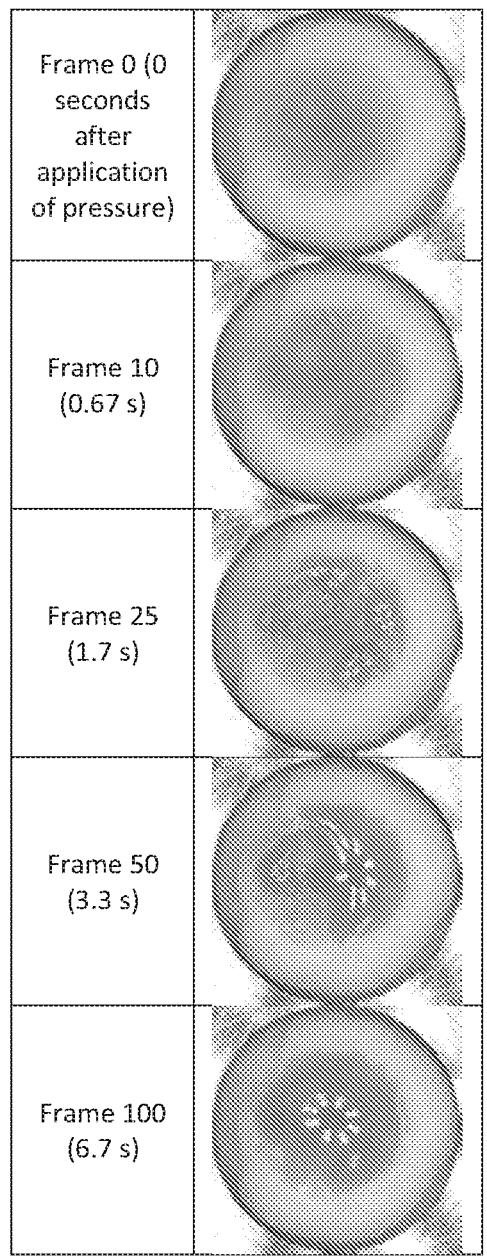
FIG. 10 is a sequence of pictures illustrating the hydraulic conductance of a dentin section according to an embodiment of the invention.

As shown in FIG. 10, a frame sequence showing progressive appearance of liquid atop an untreated dentin surface and FIG. 11A, after preparation via the etching and conditioning procedures, a dentin section was subjected to baseline hydraulic conductance and video photography measurements detailed above. The dentin section was then subjected to three treatments with a polyethylene-backed whitening strip coated with about 0.2 mm of adhesive gel, formulated to interact with dentin. Each treatment procedure was preceded by replacement of the fluid source with simulated pulpal solution, including flushing the bottom component of the test cell through the flush channel, closing the effluent valve on the flush channel, and application of modest fluid pressure to the test cell by elevating the fluid source 30 cm above the cell. Using an arch punch applied to an inverted strip (gel side up), a disk was made having a diameter matching that of the exposed dentin surface (9.5 mm) The disk was applied to the dentin section gel side down, and centered to ensure direct contact between the gel of the whitening strip and the dentin section. The dentin sections were treated for 10 minutes. Following treatment, the disk was removed, and the dentin section rinsed with Hartmanns solution.

Measurement of post-treatment hydraulic conductance was conducted after each treatment procedure, and was preceded by replacement of the fluid source with Hartmanns solution, including flushing the bottom component of the test cell through the flush channel, closing the effluent valve on the flush channel, and application of 30 psi fluid pressure to the test cell. A video sequence of the post-treatment flow was also captured in the same treated section after 3 treatment procedures.

As shown in FIGS. 11A and 11B, the method was able to show the effect of three successive applications of a whitening strip on the hydraulic conductance of the dentin section. The effect was visually recorded demonstrating reduction in hydraulic conductance of the whitening strip treated dentin section as compared to the untreated dentin section. In order to accommodate the 2-dimensional format of FIGS. 11A and 11B, a still frame was extracted from video photography of each of the treated sections. However, the full video sequence may also be utilized in cases wherever the capability to display digital media is available. At a collection rate of 15 frames per second, frame 100 corresponds to 6.7 seconds after pressure application. In this illustrative example, a single dentin section was used. However, it may be desirable to collect quantitative hydraulic conductance data from several dentin sections to ascertain section-to-section variability and to ensure that the rate of fluid appearance in the photographed section is not atypically high or low before treatment, and to ensure that the flow reduction after treatment is likewise not atypically high or low.

Comparative Results: Quantitative Hydraulic Conductance

Comparative results for hydraulic conductance were calculated as % reduction in hydraulic conductance as per the equation shown below:

$$\% \text{ Reduction} = 100 \frac{(Q_p - Q_b)}{Q_b} \quad (2)$$

Where $Q_p$=post-treatment hydraulic conductance, and $Q_b$=baseline hydraulic conductance.

Example 2: Comparison

The method is also able to visually record the effects of various oral care compositions and treatments on hydraulic conductance of dentin sections; allowing a viewer to distinguish the effectiveness of such oral care compositions and treatments on reducing or blocking dentin hydraulic conductance.

Treatment

After preparation via the etching and conditioning procedures, a dentin section was subjected to baseline hydraulic conductance and video photography measurements detailed above prior to multiple treatments with a commercially-available antisensitivity dentifrice containing calcium phosphosilicate (Sensodyne Repair & Protect Whitening toothpaste, GlaxoSmitKline, lot 313E L2, Philadelphia, Pa.). Each treatment procedure was preceded by replacement of the fluid source with simulated pulpal solution, including flushing the bottom component of the test cell through the flush channel, closing the effluent valve on the flush channel, and application of modest fluid pressure to the test cell by elevating the fluid source 30 cm above the test cell. Treatment was initiated by applying a pea-sized (0.20 cm$^3$) quantity of dentifrice onto an ADA standard reference toothbrush (Ranir Corp p/n 101044100, Grand Rapids, Mich. or CVS Pharmacy p/n 29470A). The bristle portion having the dentifrice was dipped in Hartmann's solution and the toothbrush gently tapped to remove excess liquid. The dentin section was brushed with the loaded toothbrush for about 30 seconds in a circular manner using gentle pressure (approximately 25 g), with the brush handle angled approximately 30° with respect to the dentin section surface in order to clear the top component and make contact with the dentin section. The dentin section was then rotated counterclockwise 90°, the brush momentarily rewetted in Hartmanns solution (without rinsing away the toothpaste) and the dentin section brushed an additional 30 s. A 0.20 cm$^3$ quantity of dentifrice was then reapplied to the bristle portion of the toothbrush, the dentin section rotated counterclockwise 90° and brushed again for 30 seconds. The dentin section was rotated counterclockwise another 90°, the brush momentarily rewetted, and dentin section brushed for a final 30 seconds. Using a laboratory wash bottle, a stream of Hartmanns solution was directed around the dentin section to rinse away residual dentifrice until the surface was visibly clean. Measurement of post-treatment hydraulic conductance was conducted after each treatment procedure, and was preceded by replacement of the fluid source with Hartmanns solution, including flushing the bottom component of the test cell through the flush channel, closing the effluent valve on the flush channel, and application of 30 psi fluid pressure to the test cell. A video sequence of the post-treatment flow was also captured in the same treated section after 3 treatment procedures.

FIG. 12 contains images which illustrate the relative efficacy of the whitening strip treatment described in EXAMPLE 1 (shown on the right in FIG. 12) in comparison to the dentifrice treatment in EXAMPLE 2 (shown on the left in FIG. 12). VirtualDub software (Avery Lee, v. 1.9.11) was used to crop images from video photography of the treated sections, enabling side-by-side comparisons. The picture-in-picture functionality in Camtasia Studio software was utilized to overlay video tracks of cropped images. In order to accommodate the 2-dimensional format of FIGS. 11A and 11B, frame 22 was extracted from the video sequence. The full video sequence may also be utilized in cases wherever the capability to display digital media is available. The side-by-side cropped overlay comparison is one of a number of comparisons that may be constructed from the video data, and is a particularly effective method of drawing the viewer's attention to any contrast evident in post-treatment flow of two or more sections.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of visually recording the hydraulic conductance of a dentin section, comprising:
    a) preparing a dentin section;
    b) providing a test cell having a bottom component with an inner chamber;
    c) providing a washer having a washer first surface and a washer second surface;
    d) applying adhesive to washer first surface and washer second surface;
    e) contacting adhesive and washer first surface with the bottom component;
    f) positioning at least a portion of the dentin section on the adhesive and washer second surface;
    g) providing a fluid under pressure to the inner chamber of the bottom component; and h) visually recording hydraulic conductance of fluid through the dentin section, by visually recording images of liquid droplets coalescing on the dentin section surface;
i) distinguishing individual droplets from the dentin surface using at least one of reflective lighting or magnification;
wherein the washer forms a liquid-tight seal between the bottom component and dentin section establishing fluid communication between the bottom component and denting section.

2. A method of visually comparing the effect of two or more oral care compositions on the hydraulic conductance of dentin sections, comprising:
a) preparing a first dentin section;
b) providing a test cell having a bottom component with an inner chamber;
c) providing a washer having a washer first surface and a washer second surface;
d) applying adhesive to washer first surface and washer second surface;
e) contacting adhesive and washer first surface with the bottom component;
f) positioning at least a portion of the first dentin section on the adhesive and washer second surface,
g) providing a fluid under pressure to the inner chamber of the bottom component;
h) treating at least a portion of the first dentin section with a first oral care composition;
i) visually recording hydraulic conductance of fluid through the first dentin section, by visually recording images of liquid droplets coalescing on the dentin section surface;
j) distinguishing individual droplets from the dentin surface using at least one of reflective lighting or magnification;
k) preparing a second dentin section;
l) providing a test cell having a bottom component with an inner chamber;
m) providing a washer having a washer first surface and a washer second surface;
n) applying adhesive to washer first surface and washer second surface;
o) contacting adhesive and washer first surface with the bottom component;
p) positioning at least a portion of the second dentin section on the adhesive and washer second surface;
q) providing a fluid under pressure to the inner chamber of the bottom component;
r) treating at least a portion of the second dentin section with a second oral care composition;
s) visually recording hydraulic conductance of fluid through the second dentin section, by visually recording images of liquid droplets coalescing on the dentin section surface;
i) distinguishing individual droplets from the dentin surface using at least one of reflective lighting or magnification;
t) comparing the visually recorded hydraulic conductance of the denting section treated with the first oral care composition and the second dentin section treated with the second oral care composition
wherein the washer forms a liquid-tight seal between the bottom component and dentin section establishing fluid communication between the bottom component and denting section.

3. The method of claim 2, wherein a camera is used to visually record hydraulic conductance.

4. The method of claim 3, wherein the camera visually records hydraulic conductance of fluid through the first dentin section and second dentin section.

5. The method of claim 4, wherein the images captured by the camera during recording hydraulic conductance of fluid through the first and second dentin section are cropped to enable side-by-side comparisons.

\* \* \* \* \*